United States Patent [19]

Greco

[11] Patent Number: 4,633,022

[45] Date of Patent: Dec. 30, 1986

[54] PROCESS FOR PREPARATION OF TRISUBSTITUTED PHENOLS

[75] Inventor: Nicholas P. Greco, Pittsburgh, Pa.

[73] Assignee: Koppers Company, Inc., Pittsburgh, Pa.

[21] Appl. No.: 776,398

[22] Filed: Sep. 16, 1985

[51] Int. Cl.$^4$ .................. C07C 37/50; C07C 39/06; C07C 41/01; C07C 43/205

[52] U.S. Cl. .................. 568/660; 568/780; 568/782; 568/784

[58] Field of Search .............. 568/660, 784, 780, 782, 568/799

[56] References Cited

U.S. PATENT DOCUMENTS

| | | | |
|---|---|---|---|
| 2,838,571 | 6/1958 | Filbey | 568/662 |
| 2,841,623 | 7/1958 | Norton et al. | 568/785 |
| 3,006,969 | 10/1961 | Koetitz | 568/784 |
| 4,038,327 | 7/1977 | Brindell et al. | 568/660 X |
| 4,122,287 | 10/1978 | Zakharova et al. | 568/784 |

OTHER PUBLICATIONS

Sadykhov et al., Synthesis and Study of Stabilizing Agents with Paired Reactive Sites etc., Chem. Abs. (1978) 89:111083m.
Chem. Abs. (1963) 1402(a).

*Primary Examiner*—Bernard Helfin
*Attorney, Agent, or Firm*—Donald M. MacKay; Herbert J. Zeh, Jr.

[57] ABSTRACT

2,6-dialkyl substituted phenols such as 2,6-ditertiary butylphenol are reacted with formaldehyde in methyl alcohol in the presence of an inert gas and a tertiary amine catalyst to produce a bis(3,5-di-t-butyl-4-hydroxybenzyl)ether; and the bis ether subjected to hydrogenolysis in the presence of a catalyst, a solvent and an amine to prepare a trisubstituted phenol such as 2,6-di-t-butyl-4-methyl-phenol.

14 Claims, No Drawings

PROCESS FOR PREPARATION OF TRISUBSTITUTED PHENOLS

BACKGROUND OF THE INVENTION

Sadykhov, Inst. Neftekhim Protsessov Akad. Nauk 9 11,5(1977) describes the preparation of:

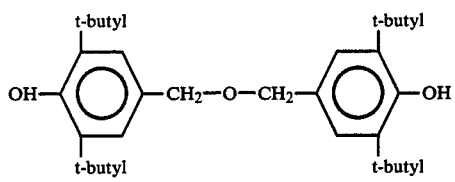

by the reaction of 2,6-di-tert-butylphenol with formaldehyde or paraformaldehyde in the presence of hydrochloric acid. The disadvantage of the process is that chloroethers are produced which are known to be carcinogens.

Belgian Pat. No. 608,758(1962) describes the preparation of (I) by reacting 3,5-di-tert-butyl 4-hydroxybenxyl alcohol in methylene chloride with dilute sulfuric acid to prepare (I) in 81% yield.

BRIEF DESCRIPTION OF THE INVENTION

The invention relates to a process for the preparation of trisubstituted phenols of the formula:

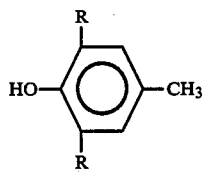

wherein the R groups are the same or different and are selected from 1 to 12 carbon alkyl, which comprises reacting a 2,6-dialkyl substituted phenol of the formula:

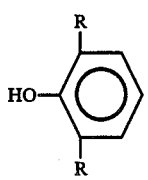

wherein the R groups are as previously defined, with formaldehyde and a tertiary amine catalyst of from 1 to 36 carbon atoms in a solvent consisting essentially of methyl alcohol and in the presence of an inert gas, wherein the amine is present in a catalytic amount and said phenol and formaldehyde are present in substantially equimolar amounts, for a time and temperature sufficient to form a bis ether of the formula:

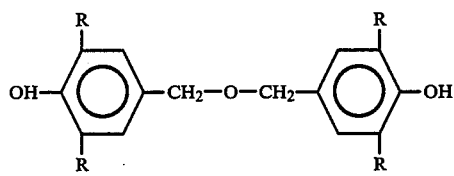

wherein the R groups are as previously defined. The bis ether is then subjected to hydrogenolysis in the presence of a hydrogenolysis catalyst, amine, and solvent at a temperature between about 50° C. and about 160° C. at a pressure of between about 5 psi and about 500 psi of hydrogen for a time sufficient to prepare the phenol.

DETAILED DESCRIPTION OF THE INVENTION

As used herein, the term formaldehyde includes paraformaldehyde methyl formcel and aqueous formaldehyde solution.

Suitable phenols for making the bis ether are those having 1 to 12 carbon alkyl in the positions ortho to the hydroxyl group. Typical examples include 2,6-di-tert-butyl-phenol, 2,6-di-dodecyl phenol, 2-methyl, 6-tert-butyl phenol, 2,6-dodecyl phenol, 2,6-dicyclohexyl phenol, 2,6-dimethyl phenol, 2,6-diethyl phenol, 2,6-di-n-propyl phenol, 2,6-diamyl phenol, 2,6-dihexyl phenol, 2,6-dioctyl phenol and the like.

Suitable tertiary amine catalysts include those having from 1 to 36 carbon atoms. Typical examples are trimethyl amine, triethyl amine, tripropyl amine, triisobutyl amine, tributyl amine, trihexyl amine, tricyclohexyl amine, trioctyl amine, tridecyl amine, tridodecyl amine and tribenzyl amine, and triethylenediamine. Exemplary of suitable inert gases are nitrogen, argon and helium.

In order to obtain little or no by-products, the bis ether reactants are employed in an equimolar basis with a catalytic amount of about 0.1 to 1.0 mole of tertiary amine per mole of phenol.

The bis ether reaction can be conveniently conducted at a temperature between about 70° C. and about 140° C., and preferably between about 70° C. and about 120° C., at a pressure of from about 1 to about 5 atmospheres.

The bis ether can be isolated by filtration and subjected to hydrogenolysis or the reaction mixture can be subjected to hydrogenolysis if an amine is present. The hydrogenolysis of the bis ether can be conveniently conducted at a temperature between about 50° C. and about 160° C., preferably between about 100° C. and about 130° C., and at a pressure between about 5 and about 500 psi of hydrogen, preferably between about 200 and 400 psi of hydrogen. The hydrogenolysis reaction conditions are not critical, however. The hydrogenolysis can be conducted in a batch or continuous operation for a time sufficient that hydrogen absorption has ceased.

Hydrogenolysis catalysts which can be employed include nickel, copper chromite, palladium, platinum, rhodium, ruthenium, and the like, but nickel is preferred. The amount will depend on the catalyst employed but generally from 0.3 to 10% by weight of the bis compound will be sufficient.

The amine which prevents the hydrogenolysis from being carried too far, need not be a tertiary amine as employed to make the bis ether. Thus, primary, secondary or tertiary amines may be employed. Suitable secondary amines include piperidine, diethyl amine, dicyclohexyl amine, dibutyl amine, and dimethyl amine. Suitable primary amines include methyl amine, ethyl amine, propyl amine, butyl amine, tert-butyl amine, xylilidene amine, cyclohexyl amine, and methylcyclohexyl amine. Exemplary of suitable tertiary amines are those used for the catalyst.

Suitable solvents for the preparation of the bis ether are those inert liquids in which the reactants, and preferably the product, are soluble. Water which is formed in the reaction should be soluble in the solvent to prevent retarding the activity of the catalyst. Typical solvents include: methyl alcohol, ethyl alcohol, isopropyl alcohol, tert-butyl alcohol, n-butyl alcohol, sec-butyl alcohol, dioxane, ethylene glycol, propylene glycol, cyclohexanol, and alcohol solution of heptane. Preferred hydrogenolysis solvents are the 1 to 4 carbon alcohols such as methyl alcohol, ethyl alcohol, isopropyl alcohol, and tert-butyl alcohol; and isopropyl alcohol is most preferred. Some methyl alcohol is required in order to obtain high yields. Generally about 1 mole per mole of trisubstituted phenol is enough.

The following examples will serve to illustrate the invention and preferred embodiments thereof. All parts and percentages in said examples, and elsewhere in the specification and claims, are by weight unless otherwise indicated.

EXAMPLE 1

2,6-di-t-butylphenol (206 g, 1 mole), methyl alcohol (500 ml, 12 moles) paraformaldehyde (36 g, 1.0 mole 95% purity) and triethyl amine (125 ml, 0.9 mole) were refluxed at about 70° C. at atmospheric pressure for 16 hrs. under a nitrogen blanket. About 250 ml of methyl alcohol and triethylamine mixture were distilled at 63°–65° C. from the reaction mixture which was then allowed to cool to room temperature. The crystallized product was filtered and washed five times on the filter with 50 ml portions of methyl alcohol. The bis(3,5-di-t-butyl-4-hydroxbenzyl)ether product was air dried to give 223 g. Analysis by gas chromatography (GC) showed the product to be 96.5% pure. The filtrates were combined and distilled to remove the methyl alcohol and triethylamine to give 10.5 g more of product with a purity of 52%. The total yield of product was 98 mole %.

Prior Art Comparison
EXAMPLE 2

The general procedure of Example 1 was repeated but for the exception that an alkaline catalyst comprising a buffer of sodium carbonate and sodium bicarbonate was employed for triethyl amine. The yield was only 58%.

Prior Art Comparison
EXAMPLE 3

The general procedure of Example 1 was repeated but for the exception that sodium hydroxide was employed as the catalyst in lieu of triethyl amine. The yield of product was only 50%.

EXAMPLE 4

A 2 l. pressure reactor charged with 2,6-di-t-butylphenol (206 g, 1.0 m), methyl alcohol (396 g, 12 m), paraformaldehyde (30 g, 1.0 m), and triethylamine (91 g, 0.9 m) was heated at 90° C. for 5 hrs under a nitrogen blanket at atmospheric pressure. The mixture was transferred to a 1 gallon stirred reactor, a nickel catalyst (10 g) added and hydrogen pressured into the reactor to 300 psig. The reactor was heated at 130°–135° C. until absorption of hydrogen ceased after about 0.5 hrs.

The product was filtered to remove the catalyst and the methyl alcohol and triethylamine was distilled off. The distillation residue of crude 2,6-di-t-butyl-4-methylphenol (DBPC) (230 g) by GC analysis was 89% DBPC and 1.6% 2,6-di-t-butylphenol. Distillation through a 36"×1¼" packed column b.p. 106°–108° C./3–4 mm $H_g$ gave 203 g (92 mole % yield) of DBPC.

EXAMPLE 5

A 2.5 liter shaker reactor was charged with 2,6-di-t-butylphenol (52 g, 0.25 m), formaldehyde (21 g of 37% aq. solution, 0.25 m), triethylamine (30 g, 0.3 m) and methyl alcohol (200 ml). The mixture was heated at 127° C. for 2 hrs. under a nitrogen blanket with agitation. The mixture was hydrogenated at 160° C. in the presence of nickel catalyst (5 g) and 300 psig of $H_2$. Absorption of hydrogen ceased after 15 minutes. The product, after filtering to remove the catalyst, was distilled to recover methyl alcohol, triethylamine and crude DBPC which was distilled at 128° C./6–8 mm $H_g$ to give 51 g (93 mole % yield) of DBPC. Analysis of DBPC by GC was 97% DBPC and 2.8% 2,6-di-t-butylphenol.

While the above examples are illustrative of preferred embodiments of the invention, the other materials and conditions listed in the specification can be employed with similar results. Moreover, numerous obvious variations will occur to one of ordinary skill, and accordingly, the invention is intended to be limited only by the appended claims.

What is claimed is:

1. A process for the preparation of bis ethers of the formula:

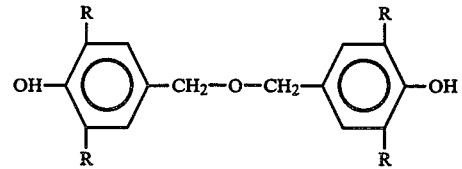

wherein the R groups are the same or different 1 to 12 carbon alkyl, which comprises reacting a 2,6-dialkyl substituted phenol of the formula:

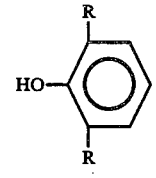

wherein the R groups are as previously defined, with formaldehyde in the presence of an inert gas, a solvent consisting essentially of methyl alcohol, and a tertiary amine catalyst wherein the phenol and formaldehyde are present in substantially equimolar proportions and the tertiary amine is present in a catalytic amount.

2. The process of claim 1 wherein formaldehyde, and 2,6-ditertiary butylphenol are reacted in equimolar amounts in methyl alcohol in the presence of a catalytic amount of triethylamine to produce bis(3,5-di-t-butyl-4-hydroxybenzyl)ether.

3. The process of claim 1 wherein the temperature of the reaction is maintained between about 70° C. and about 140° C.

4. The process of claim 1 wherein the temperature is maintained between about 70° C. and about 120° C.

5. The process of claim 1 wherein the pressure is from about 1 to about 5 atmospheres.

6. A process for the preparation of trisubstituted phenols of the formula:

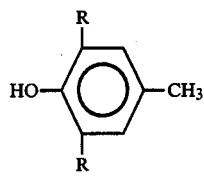

wherein the R groups are the same or different and are selected from 1 to 12 carbon alkyl, which comprises hydrogenolysis of a bis ether of the formula:

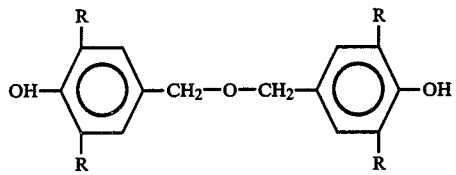

wherein the R groups are as previously defined, in the presence of a catalyst, an amine and a solvent at a temperature between about 100° C. and about 160° C. at a pressure between about 5 psi and about 500 psi of hydrogen for a time sufficient to prepare said phenol.

7. The process of claim 6 wherein the pressure is between about and about 400 psi of hydrogen.

8. The process of claim 6 wherein the solvent is isopropyl alcohol.

9. The process of claim 6 wherein the amine is present in an amount between about 0.1 to 1.0 mole per mole of bis ether.

10. A process for the preparation of trisubstituted phenols of the formula:

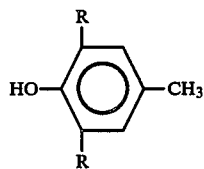

wherein the R groups are the same or different and are selected from 1 to 12 carbon alkyl, which comprises reacting a 2,6-dialkyl substituted phenol of the formula:

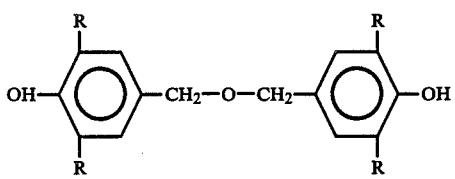

wherein the R groups are as previously defined, with formaldehyde in the presence of an inert gas, a solvent consisting essentially of methyl alcohol, and a tertiary amine catalyst wherein the phenol and formaldehyde are present in substantially equimolar proportions and the tertiary amine is present in a catalytic amount, to form a bis ether of the formula:

wherein the R groups are as previously defined, and subjecting said bis ether to hydrogenolysis in the presence of a hydrogenolysis catalyst, an amine over hydrogenolysis inhibitor and a solvent at a temperature between about 100° C. and about 130° C. at a pressure between about 5 psi and about 500 psi of hydrogen for a time sufficient to prepare said trisubstituted phenol.

11. The process of claim 10 wherein formaldehyde, and 2,6-ditertiary butylphenol are reacted in equimolar amounts in methyl alcohol in the presence of a catalytic amount of triethylamine to produce bis(3,5-di-t-butyl-4-hydroxybenzyl)ether.

12. The process of claim 11 wherein the temperature of the reaction is maintained between about 70° C. and about 140° C.

13. The process of claim 11 wherein the temperature is maintained between 70° C. and about 120° C.

14. The process of claim 10 wherein the hydrogenolysis catalyst is nickel.

* * * * *